United States Patent [19]

Carson

[11] 4,139,573
[45] Feb. 13, 1979

[54] ISOPARAFFIN-OLEFIN ALKYLATION UTILIZING VAPORIZATION OF NORMAL PARAFFIN TO CONTROL THE REACTION TEMPERATURE

[75] Inventor: Don B. Carson, Mt. Prospect, Ill.

[73] Assignee: UOP Inc., Des Plaines, Ill.

[21] Appl. No.: 899,753

[22] Filed: Apr. 24, 1978

[51] Int. Cl.² ................................................. C07C 3/54
[52] U.S. Cl. ................................................. 260/683.49
[58] Field of Search ...................... 260/683.48, 683.49, 260/683.58, 683.59, 683.61, 683.62

[56] References Cited

U.S. PATENT DOCUMENTS

| 2,409,389 | 10/1946 | Ringham ........................ 260/683.45 |
| 2,906,796 | 9/1959 | Putney ........................... 260/683.48 |
| 2,949,494 | 8/1960 | Putney ........................... 260/683.58 |
| 3,055,958 | 9/1962 | Webb, Jr. ...................... 260/683.58 |
| 3,080,438 | 3/1963 | Sailors ........................... 260/683.48 |
| 3,105,102 | 9/1963 | Webb, Jr. ...................... 260/683.58 |
| 3,969,078 | 7/1976 | Zabransky ...................... 260/683.48 |
| 3,981,942 | 9/1976 | Zabransky ...................... 260/683.48 |

Primary Examiner—George Crasanakis
Attorney, Agent, or Firm—James R. Hoatson, Jr.; Robert W. Erickson; William H. Page, II

[57] ABSTRACT

Uniform reactor temperature and temperature control of an HF acid-catalyzed reactant mixture of isobutane and an olefinic feed stream is achieved through indirect vaporization of a liquefied hydrocarbon by the reaction mixture. The exothermic heat of reaction is utilized to effect a fractional distillation. This concept and technique obviates the need for a water-cooled exchanger, thereby eliminating the possibility of HF-acid contamination of water bodies.

10 Claims, 1 Drawing Figure

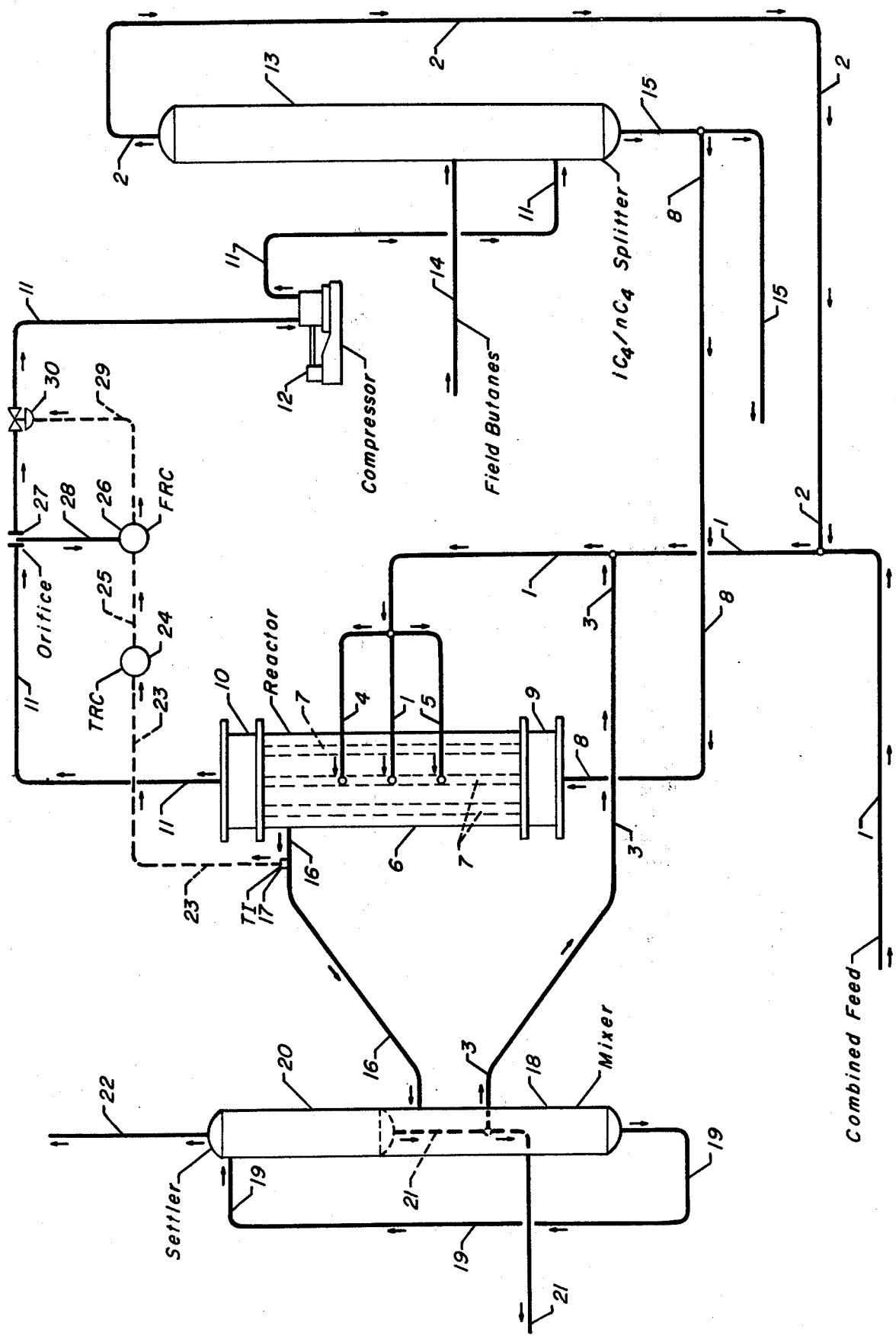

ISOPARAFFIN-OLEFIN ALKYLATION UTILIZING VAPORIZATION OF NORMAL PARAFFIN TO CONTROL THE REACTION TEMPERATURE

APPLICABILITY OF INVENTION

As described herein, the present inventive concept directs itself to, and encompasses a process for effecting the HF-acid catalyzed reaction of an isoparaffin with an olefin to produce a normally liquid motor fuel alkylate. Such a reaction was developed more than 35 years ago in order to meet the ever-increasing demands for staggering quantities of high-octane motor fuels having enhanced anti-knock properties. Since the advent thereof, the HF alkylation process has experienced a multitude of changes and improvements with respect to unit design and operating techniques. Suitable isoparaffins are those having four to about seven carbon atoms per molecule, including isobutane, isopentane, neopentane, one or more isohexanes and various isoheptanes. Similarly, the olefinic feed stream contains from three to about seven carbon atoms per molecule, and includes propylene, 1-butene, 2-butene, isobutylene, the isomeric amylenes, hexenes, heptenes and mixtures. For all practical purposes, the greater majority of HF alkylation processes employ isobutane with the olefinic material being either propylene, butylenes, or mixtures thereof.

Many innovations in HF alkylation have been directed toward the cooling of the reaction mixture. Such is mandatory due to the exceptionally high degree of exothermicity which accompanies alkylation reactions. An anomaly exists since lower reaction mixture temperatures — e.g. 50° F. to 70° F. — versus the more commonly employed higher temperature of around 100° F. creates significantly more favorable results. As an example, alkylate product quality is improved; high molecular weight polymeric material (commonly referred to as "tar") formation is inhibited and reduced; and, the isobutane to olefin ratio in the reaction chamber can be reduced. In its basic conceptual form, the present invention directs itself not only at this desirable reduction in reaction mixture temperature, but also at the advantageous utilization of the exothermic heat of reaction which is wasted in conventional designs.

OBJECTS AND EMBODIMENTS

A principal object of the present invention is to provide a method for controlling the temperature of the reaction mixture in HF-acid catalyzed alkylation of an isoparaffin with an olefin. As a corollary objective, the control of HF alkylation reaction temperature is achieved in a more economical, trouble-free fashion.

Another object is to make possible the control of the reactor temperature at a level lower than that which could be achieved through the use of ambient temperature air or water as a reactor cooling medium.

Specifically, an object is to afford reduced capital investment and operating costs with respect to major vessels, equipment and off-site facilities associated with acid-catalyzed alkylation systems.

Therefore, in a broad embodiment, the present invention affords a process for the acid-catalyzed alkylation of an isoparaffin with an olefinic feed stream which comprises the steps of: (a) separating an isoparaffin/normal paraffin mixture in a separation zone, at separation conditions selected to provide (i) an isoparaffin concentrate and, (ii) a normal paraffin concentrate; (b) reacting said isoparaffin concentrate with said feed stream in admixture with an acid-acting catalyst, in a reaction vessel and at alkylation conditions selected to produce a normally liquid alkylate product; (c) introducing a liquefied portion of said normal paraffin concentrate into said reaction vessel, and therein vaporizing said normal paraffin via indirect contact with the isoparaffin/olefinic reaction mixture; and, (d) increasing the pressure of the resulting normal paraffin vapors and introducing the same into said separation zone.

In another embodiment, my inventive concept encompasses a process for the acid-catalyzed alkylation of an isoparaffin with an olefin, wherein the method of controlling the temperature of the reaction mixture within the alkylation reaction zone comprises the sequential steps of: (a) introducing a liquefied hydrocarbon into said alkylation reaction zone and therein vaporizing said hydrocarbon via indirect contact with said reaction mixture; (b) sensing the temperature of said reaction mixture, comparing the sensed temperature with that specified by the adjustable set point of a temperature controller and developing an output signal representing the resulting comparison; and, (c) regulating the quantity of said liquefied hydrocarbon introduced into said alkylation reaction zone in response to said output signal.

This embodiment is further characterized in that the liquefied hydrocarbon is a paraffin which is vaporous at normal conditions of 60° F. and atmospheric pressure.

In a more specific embodiment, the present invention is directed toward a process for alkylating isobutane with an olefinic feed stream which comprises the sequential steps of: (a) reacting said isobutane with said feed stream, in admixture with a hydrogen fluoride catalyst, in an alkylation reaction zone, at alkylating conditions resulting in a reaction product effluent; (b) introducing normal butane into said reaction zone and therein vaporizing said normal butane via indirect contact with the reaction mixture of hydrogen fluoride, isobutane and said olefinic feed stream; (c) sensing the temperature of said reaction mixture, comparing said temperature with that temperature specified by the adjustable set point of a temperature controller and developing a first output signal representing the resulting comparison; (d) withdrawing vaporized normal butane from said alkylation reaction zone and introducing said vaporized normal butane, at increased pressure, into a fractionation facility into which a mixture of isobutane and normal butane is also introduced; (e) recovering separated streams of isobutane and normal butane, liquefying at least a portion of said normal butane and recycling the same to said alkylation reaction zone; and, (f) transmitting said first output signal to a flow controller having an adjustable set point which is adjusted responsive to said first signal, developing a second output signal representative of the resulting adjustment and regulating the quantity of said liquefied normal butane in response to said second signal.

Other objects and embodiments of my invention will become evident from the following more detailed description thereof. In one such other embodiment, the olefinic feed stream comprises propylene, butylenes, or a mixture thereof.

CITATION OF RELEVANT PRIOR ART

Candor compels recognition and acknowledgment of the fact that the prior art is replete with a wide variety of publications, inclusive of issued patents, directed toward the acid-catalyzed alkylation of an isoparaffin with an olefin to produce a normally liquid alkylate motor fuel product. This is particularly true with respect to hydrogen fluoride alkylation which traces its development over an approximate 35-year period. Any attempt to exhaustively delineate the HF alkylation art herein would constitute an exercise in futility. However, a brief description of six innovations, for the purposes of illustrating the particular area to which the present invention is applicable, is believed to be warranted. Copies of the six specifically delineated United States Patents accompany this application.

U.S. Pat. No. 3,080,438 (Cl. 260-683.48), issued March 5, 1963, is principally directed toward HF alkylation effected in a so-called circulatory system wherein the hydrocarbon portion of the reactant stream becomes the continuous phase. A relatively large amount of the hydrocarbon phase recovered from the alkylation effluent (alkylate product and unreacted isobutane) is cooled and introduced into an acid cooler containing mixing means. The rate of the cooling medium employed to cool the portion of hydrocarbon product is regulated in direct response to the temperature sensed in the reaction conduit. The thus-cooled product, in admixture with fresh hydrocarbon charge stock is passed through the internal mixer, thereby picking up hydrogen fluoride from the surrounding volume in the acid cooler (Column 3, Lines 59-64). HF acid is withdrawn from a settler (17) on a ratio flow control, which also monitors the flow rate of the hydrocarbon feed, for introduction into the acid cooler.

It would appear that the greater proportion of the heat of reaction is removed by the voluminous portion of the cooled product hydrocarbon phase withdrawn from the settler (Column 4, Lines 48-52). This is nothing more than introducing the fresh feed (Lines 10 and 11) at a reduced temperature. The principal purpose for recycling the large quantity of product hydrocarbon is to create a hydrocarbon continuous phase and to improve the ultimate product quality.

A control system for regulating reaction zone temperature is presented in U.S. Pat. No. 3,981,942 (Cl. 260-683.48), issued Sept. 21, 1976, and is directed specifically to HF alkylation units having a mixed olefinic charge which is susceptible to fluctuations in composition. Essentially, the composition of the feed stream is analyzed, the octane rating of the ultimate alkylate product is determined and the temperature of the reaction mixture is sensed. Representative signals are developed and transmitted to computer/comparator means. The latter generates two signals, one of which is used to regulate the quantity of effluent recycle (line 42 from settler 13), the second being the regulation of the reactor cooling medium (line 9).

Cumulative to No. 3,981,942 are the following U.S. Pats.: No. 3,929,926 (Cl. 260-683.48), issued Dec. 30, 1975; No. 3,937,749 (Cl. 260-683.48), issued Feb. 10, 1976; No. 3,948,603 (Cl. 23-253A), issued Apr. 6, 1976; No. 3,969,078 (Cl. 23-253A), issued July 13, 1976; and, No. 3,972,957 (Cl. 260-683.48), issued Aug. 3, 1976. Copies of these cumulative patents have not been filed with this application.

In U.S. Pat. No. 2,409,389 (Cl. 260-683.45), issued Oct. 15, 1946, alkylation of an isoparaffin with an olefin is effected utilizing a liquid hydrocarbon/aluminum chloride catalyst. A plurality (four) of reaction vessels are used in conjunction with a plurality of settlers (three). Alkylate-containing product (line 55) is introduced into separating means (60), from which di-isopropyl product (line 62), light gases (line 66), heavy alkylate (line 65), isobutane (line 63) and normal butane (line 64) are recovered. The isobutane is recycled to the alkylation system, while the normal butane is withdrawn therefrom. Normal butane enters the process with the combined feed stream (line 11) and the make-up isobutane stream (line 10). Use of the normal butane stream in accordance with my inventive concept is not recognized.

U.S. Pat. No. 3,867,473 (Cl. 260-683.45), issued Feb. 18, 1975, directs itself to a two reaction vessel system (5 and 14) in which all the isobutane (lines 4 and 30) is introduced into the first zone, whereas the olefinic feed stream is split (lines 2 and 3). An isostripping column is employed to recover alkylate product and isobutane for recycle, reject a propane concentrate and remove normal butane from the system (line 29). Reaction mixture temperature in both reaction vessels is maintained by absorbing the exothermic heat of reaction with cooling water (lines 6 and 15).

U.S. Pat. No. 2,906,796 (Cl. 260-683.48), issued Sept. 29, 1959, is directed toward a two-stage process for acid alkylation of an isoparaffin with an olefinic feed stream. Applicable to both $H_2SO_4$-acid (FIG. 1) and HF-acid (FIG. 2) techniques, the process utilizes a closed cycle refrigeration system to cool one of the reaction stages and so-called "effluent refrigeration" to cool the second reaction stage. The former is acknowledged as old in the art, and utilizes ammonia or propane (Column 3, Lines 15-28). Effluent refrigeration is defined (Column 1, Lines 24-33) as any system employing all, or part of the product effluent issuing from a reaction vessel, or from the acid settler. With respect to FIG. 2, the effluent refrigeration technique is described at Column 10, Line 32 through Column 11, Line 12. Similarly, U.S. Pat. No. 2,949,494 (Cl. 260-683.58), issued Aug. 16, 1960, utilizes all of the hydrocarbon-rich reaction product effluent, at a reduced pressure, (after acid separation), as the reaction zone cooling medium.

Molecular sieve separation of normal paraffins, introduced into the alkylation system with the isoparaffin feed, for the removal thereof from the process, is the subject of U.S. Pat. No. 3,105,102 (Cl. 260-683.58), issued Sept. 24, 1963. It should be noted that the separation takes place after the normal paraffin has passed through the reaction zone as a component of the reaction mixture, and following the separation of the HF-acid from the reaction product effluent. The cooling medium thus includes (FIG. 1) the normally liquid alkylate product. In FIG. 2, the molecular sieve separation is effected after the hydrocarbon-rich portion of the reaction product effluent has been utilized as the indirect cooling medium. Closed cycle refrigeration, without identification of either the cooling medium, or the source thereof is used in the technique presented in FIG. 4.

U.S. Pat. No. 3,055,958 (Cl. 260-683.58), issued Sept. 25, 1962, offers an alleged improvement in the type of processes described in the last three delineated references. This improvement consists of an effluent (acid lean) flash system installed upstream from the commonly-utilized deisobutanizer. Flashed isobutane concentrate is condensed and re-introduced into the reaction vessel, while normal butane is removed in the deisobutanizer bottoms stream in admixture with the normally liquid alkylate product.

In the foregoing delineated references, and particularly the last four which have been described, there is no recognition of the combination of (1) separating an isoparaffin feed stream, in a separation zone, to remove normal paraffins, (2) introducing a liquefied portion of the normal paraffin into the reaction zone and therein vaporizing the same via indirect contact with the reaction mixture and, (3) increasing the pressure of the normal paraffin vapors and introducing the same into the separation zone. Actually, the foregoing represents the type of HF alkylation processes to which the present invention is applicable.

SUMMARY OF INVENTION

As hereinbefore stated, the present invention is intended to be integrated into an acid-catalyzed alkylation unit for the production of a normally liquid motor fuel alkylate (having seven or eight carbon atoms per molecule). In the interest of brevity, the invention and process will be further described with respect to the alkylation of isobutane with an olefinic feed stream containing both propylene and mixed butylenes, and utilizing hydrofluoric acid catalyst. Since both internal (isobutane recycle) and external (field butanes) streams, including the olefinic charge say from a coking unit, will contain some paraffinic material, such will appear in the reaction mixture. Hydrogen fluoride is utilized in an amount sufficient to provide an acid/hydrocarbon volume ratio, in the reaction vessel, of from about 0.5:1.0 to about 3.0:1.0. Generally, commercially available anhydrous hydrogen fluoride will be charged to the alkylation system as fresh catalyst. It is possible to use hydrogen fluoride containing as much as about 10.0% water; however, excessive dilution is undesirable since it tends to reduce the activity of the catalyst while introducing severe corrosion problems into the system.

To reduce the tendency of the olefinic components of the feedstock to undergo polymerization prior to alkylation, the molar proportion of isoparaffin to olefinic hydrocarbon within the reaction zone is maintained at a value greater than 1.0:1.0, up to about 20.0:1.0, and preferably from about 3.0:1.0 to about 15.0:1.0. Other alkylation conditions include temperatures in the range of about 0° F. ($-17.8°$ C.) to about 200° F. (93° C.); maximum temperatures are preferably not above 110° F. (43° C.) and the minimum temperature is at least about 30° F. ($-1.1°$ C.). Alkylation pressures are sufficiently high to maintain the reaction mixture in liquid phase; that is, from about 15.0 psi. (1.05 kg/sq.cm.) to about 600 psi. (42.2 kg/sq.cm.). Contact time in the alkylation reaction vessel is conveniently expressed in terms of a space-time relationship which is defined as volumes of HF-acid catalyst within the reaction zone divided by the volume rate per minute of hydrocarbon reactants charged to the reaction zone. The space-time relationship will be less than about five minutes, and preferably less than about two minutes.

It is understood that the precise operating conditions employed for a given alkylation system is not limiting upon the present invention which directs itself to a unique technique of controlling and maintaining the temperature of the reaction mixture. Hydrocarbon alkylation reactions are highly exothermic, and every conceivable means is employed to maintain and control the reaction mixture temperature at that level which is consistent with the character of the reactant feed, other operating conditions and the desired quality of the ultimate alkylate product. Where the isoparaffin is isobutane and the olefinic feed stream is a mixture of propylene and the butylenes, the precise temperature at which the reaction mixture will be best maintained is principally dependent upon the propylene/butylene ratio as well as the 1-butene/2-butene/isobutene ratio.

Alkylation reaction vessels are designed along lines similar to tube-and-shell heat-exchangers; the reaction mixture, including the HF-acid, traverses the shell side, while a cooling medium traverses the tube side in one or more passes. In a few alternative designs, only the HF-acid phase passes through the heat-exchanger in amounts so great that subcooling of this acid phase will inhibit the temperature rise in the subsequent reaction zone. In this type of system, the reaction zone may simply be a pipe or small pressure vessel. Thus, HF-acid from the acid settler passes into the cooler, the isobutane/olefinic feed is admixed with the cooled HF-acid and the mixture reintroduced into the acid settler.

Many intricate designs have been proposed, both from the standpoint of the removal of the heat of reaction and intimate mixing of the reactant stream components and the HF acid. Regardless of the vessel design employed, the cooling medium functions via indirect contact with the reaction mixture. A perusal of the prior art indicates that most commercialized alkylation systems utilize refinery cooling water to absorb the exothermic heat of reaction in maintaining reaction temperature. In general, the available refinery cooling water is at best "warm"; that is, at some temperature in excess of about 60° F., say about 80° F. to about 95° F. Since the exit temperature of the water employed to remove the exothermic heat of reaction is limited by the maximum temperature at which the reaction is to be conducted, and since the maximum temperature is desirably low, the quantity of heat removed by a given amount of cooling water is limited to the sensible heat available over a small temperature rise. Thus, extremely large quantities of cooling water are required in order to maintain the reaction mixture at its lowest possible temperature.

As a general rule, the quality of the final normally liquid alkylate product is limited by the cooling water inlet temperature. That is, alkylate quality improves with decreasing reaction mixture temperature. Obviously, the reaction mixture temperature cannot be less than the cooling water inlet temperature; at best, the minimum reaction temperature will approach the cooling water inlet temperature only within about 10° F. to about 20° F.

The process and control system encompassed by the present inventive concept, is founded upon recognizing (1) the inadequacies attendant the utilization of available refinery cooling water in voluminous quantities and, (2) that a readily-available material exists which can be substituted to significant economic and technical advantages. Considering those HF alkylation systems in which the isoparaffin is isobutane, two primary sources of isobutane supply exist. The first source is commonly referred to as "make-up isobutane", and which may be obtained as an item of commerce, subject to availability. Secondarily, isobutane is a major component of other refinery streams which are referred to in the HF alkylation art as "field butanes". Briefly referring to U.S. Pat. No. 3,981,942, hereinbefore described, the field butane stream (line 20) is introduced into the isostripping column (vessel 19), for separation therein along with the hydrocarbon-rich portion of the alkylation product effluent stream (line 18). The normal butane portion of the field butane stream is removed from the process (line 21), while the isobutane portion is recycled (line 2) to the alkylation reaction zone.

In accordance with the present invention, the field butane stream otherwise introduced and separated in the isostripping column passes into a separate isobutane/normal butane splitter. Isobutane is recovered as an overhead stream, while the normal butane is withdrawn as the bottoms stream. A portion of the latter, in its liquid state, is reduced in pressure and introduced into the tube side of the reaction vessel as aforesaid. Excess normal butane is removed from the process system as necessary. Vaporized normal butane from the reaction vessel is recovered and compressively recycled to the isobutane/normal butane splitter. Regulation of the quantity of normal butane which is necessarily introduced into the reaction vessel is accomplished by the control system hereinafter described.

A number of advantages and beneficial results arise from the use of the liquefied normal butane as above set forth; these may be categorized as both technical and economical. For example, the addition of another vessel — the isobutane/normal butane splitter — to the process is significantly more than offset by the need for a smaller reaction vessel and a smaller, less intricate isostripping column. Also, on a weight basis per unit of time, less hydrocarbon is circulated than the quantity of cooling water required to assure removal of sufficient heat of reaction to maintain the desired reaction mixture temperature. With respect to alkylate product quality, the same is improved in view of the fact that lower reaction mixture temperatures are afforded. Furthermore, lower reaction zone temperatures lead to lower heat loads on various equipment and offer savings by virtue of lower utilities cost. The compressed exiting butane vapors may or may not contain sufficient heat to operate the $iC_4/nC_4$ splitter without the need for any type of external reboiler, depending upon the compositions and amounts of the olefinic feed stream and the field butane stream. Similarly, the cost of utilities respecting the isostripper column is decreased by virtue of the fact that the field butanes are not charged to the column. A single piece of equipment, the reactor, displaces two pieces of equipment (reactor and splitter reboiler) which would be required under current concepts. Other beneficial advantages will become evident to those having the requisite skill in the art. Although the foregoing is directed toward the use of normal butane as the liquefied hydrocarbon being vaporized in the reaction vessel, other hydrocarbons may be employed. These preferably are those hydrocarbons which are normally vaporous at atmospheric pressure and a temperature of 60° F. (15.6° C.), including propane, n-butane, i-butane, 2,2-dimethyl propane, n-butylene, i-butylene, cis and trans butylene, the butadienes and mixtures. Paraffins are preferred since the olefins can be more advantageously employed as components of the reactant stream.

In further describing my invention, and the process encompassed thereby, reference will be made to the accompanying drawing which is presented for the sole purpose of illustration. In the drawing, the process is presented by way of a simplified flow diagram in which details such as pumps, instrumentation and other controls, quench systems, heat-exchange and heat-recovery circuits, valving, start-up lines and similar hardware have been eliminated as non-essential to an understanding of the techniques involved. Utilization of such miscellaneous appurtenances, to modify the process as illustrated, will become evident to those possessing the requisite skill in the art of petroleum refining technology.

DESCRIPTION OF DRAWING

The drawing will be described in conjunction with a commercially-scaled unit designed for the alkylation of isobutane with a mixed olefinic feed stream, containing propylene, various butylenes and amylenes, in an exchanger type reaction vessel. This unit has a fresh olefinic feed charge rate of about 7,125 Bbl/day (1,149.79 moles/hr.), which feed stream has been recovered from the product effluent of a fluid catalytic cracking unit. Combined feed, inclusive of an isobutane recycle stream recovered from the alkylate-containing effluent in line 22, and the isobutane recovered from field butanes in line 2 is introduced into the alkylation reactor 6 by way of line 1 and multiple feed conduits 4 and 5. HF-acid from acid settler 20 is also passed into reactor 6. In this illustration, for the sake of simplification of the drawing, the HF-acid in line 3 is shown as being admixed with the combined feed in line 1. In a commercially designed system, the HF-acid will be directly introduced into reactor 6 to avoid premature reaction of the isobutane and olefins in line 1.

In the HF alkylation unit, of which the drawing illustrates only a part, the sources of HF include the following: 139.31 moles/hr. from the isostripping column; 220.94 moles/hr. of regenerated acid; 139.31 moles/hr. from an isostripper settler; and, 70,032 moles/hr. from settler 20, for a total acid charge to reactor 6 of 70,531.56 moles/hr. Hydrocarbon sources include: the fresh olefinic feed stream, 1149.79 moles/hr.; 451.94 moles/hr. of isobutane make-up; 386.50 moles/hr. entering with the regenerated acid stream; 9,164.31 moles/hr. of isobutane-rich recycle from the isostripping column; and, 74.3 moles/hr. from $iC_4/nC_4$ splitter column 13 via line 2. The material balance around alkylation reaction vessel 6, exclusive of the HF-acid stream, is presented in the following tabulation, with the concentrations of the various components being given in terms of moles/hr. for convenience.

In reaction vessel 6, the isobutane/olefinic hydrocarbon mole ratio is about 13.0:1.0 and the HF acid/hydrocarbon volumetric ratio is about 1.53:1.0. Reaction

TABLE

| | Reaction Vessel Material Balance | |
|---|---|---|
| Component | Charge | Effluent |
| Ethane | 1.20 | 1.20 |
| Propylene | 352.94 | — |
| Propane | 758.65 | 779.62 |
| Butylenes | 333.12 | — |
| Isobutane | 8965.48 | 8258.10 |
| N-Butane | 657.30 | 663.47 |
| Amylenes | 3.59 | — |
| Isopentane | 104.59 | 128.54 |
| N-Pentane | 0.77 | — |
| Hexane-plus | 49.20 | 704.12 |
| Polymer Products | — | 0.22 | vessel 6 is maintained at a pressure of about 233 psig. (16.9 atm.), with the HF-acid and reactant streams being introduced at a temperature of about 100° F. (37.8° C.). As hereinbefore set forth, HF alkylation of an isoparaffin/olefin reactant mixture is highly exothermic, and must be tempered through the use of a cooling medium. As generally practiced, the reaction vessel, and particularly its cooling function, is calculated and designed such that the exit temperature of the alkylated product effluent is about the same as the inlet temperature of the reactant streams; or, that the entire heat of reaction be absorbed. In this illustration, the heat of reaction is about $25.9 \times 10^6$ BTU/hour. Cooling water is available at a temperature of about 85° F. (29.4° C.), and about 10,422 gallons/minute are required to maintain the product effluent in line 16 at a temperature of about 100° F. (37.8° C.); or about $5.21 \times 10^6$ lbs/hr.

In accordance with the present invention, liquefied normal butane from line 8, in the amount of about 175,000 lbs/hr., and at a temperature of about 90° F. is introduced through header 9 and vaporized in tubes 7. Butane vapors are withdrawn from header 10 through conduit 11 at a pressure of about 30 psig., increased in pressure to about 55 psig. by compressive means 12 and introduced into $iC_4/nC_4$ splitting column 13 at a temperature of 125° F. Also introduced into splitter 13 is the field butane stream from line 14. The splitter functions to produce substantially pure isobutane in line 2, for recycle to the combined feed in line 1, and the normal butane concentrate in line 15. After diverting the necessary quantity of normal butane through line 8, the excess continues through line 15 to be removed from the system. Prior to being passed into header 9, the normal butane in line 8 is liquefied and reduced in pressure to about 30 psig.

Product effluent is withdrawn from reaction vessel 6 through conduit 16, which contains a temperature indicating means 17, and introduced into mixer/soaker 18 wherein it is maintained for a period of about eight minutes. After this holding period, the product effluent is transferred via line 19 into HF acid settler 20. Settled HF acid is removed in line 21 in the amount of about 70,253.16 moles/hr. Of this amount, 70,032 moles/hr. are diverted through line 3 to serve as acid recycle (via line 1) to reaction vessel 6. Generally, the remaining 221.6 moles/hr. is accumulated until a sufficient quantity is available for introduction into an acid regenerator (not illustrated). The alkylate-containing, hydrocarbon-rich phase from settler 20, at a temperature of about 100° F. (37.8° C.) and a pressure of about 203 psig. (14.8 atm.) is withdrawn through line 22, and consists of 10,535.05 moles/hr. of hydrocarbons and 278.62 moles/hr. of HF acid. This material is transferred to the isostripping column (not illustrated), from which the alkylate product is recovered, and HF acid and unreacted isobutane is recycled as aforesaid.

Temperature indicating means 17, located in conduit 16, senses the temperature of the reaction mixture as it is withdrawn from reaction vessel 6. A signal representing this temperature is transmitted via instrument line 23 to Temperature Recorder Controller (TRC) 24. A comparison is made with that temperature called for by the adjustable set point of TRC 24, and a signal representing the comparison is transmitted to Flow Recorder Controller (FRC) 26 via conduit 25. FRC 26 forms a flow control loop with orifice meter 27 and control valve 30, both of which are shown as being installed in conduit 11. FRC 26 senses the flow of butane vapors in line 11 through orifice meter 27 and conduit 28; the sensed flow is compared to that specified by the adjustable set point of FRC 26, and an appropriate signal is transmitted via line 29 to control valve 30, whereby the opening thereof is responsively adjusted to regulate the flow of butane vapors. The signal from TRC 24 to FRC 26 is used to re-set the adjustable set point of the latter, thus causing control valve 30 to function in response to the set point adjustment. The specific location of the flow control loop represented by FRC 26, orifice meter 27 and flow regulating valve 30 is not essential to the present invention. For example, the control loop could be installed in line 8 either before, or after the diverted butane vapors are condensed; also, the control loop could be placed in conduit 15 downstream from the point where butane vapors are diverted through line 8.

The foregoing, particularly when viewed in conjunction with the drawing, clearly demonstrates the method of effecting the present invention, as well as illustrates the benefits afforded through the utilization thereof.

I claim as my invention:

1. A process for the acid-catalyzed alkylation of an isoparaffin with an olefinic feed stream which comprises the steps of:
    a. separating an isoparaffin and a normal paraffin mixture in a separation zone at separation conditions of temperature and pressure to provide (i) an isoparaffin concentrate and, (ii) a normal paraffin concentrate;
    b. reacting said isoparaffin concentrate with said olefinic feed stream in admixture with an acid-acting catalyst, in a reaction vessel and at alkylation conditions selected to produce a normally liquid alkylate product;
    c. introducing a liquefied portion of said normal paraffin concentrate into said reaction vessel and therein vaporizing said normal paraffin via heat exchange means in said vessel in contact with the reaction mixture of step (b);
    d. increasing the pressure of the resulting normal paraffin vapors from step (c) and introducing said pressurized vapors into said separation zone, and
    e. withdrawing an alkylate product from step (b).

2. The process of claim 1 further characterized in that said normal paraffin in step (a) is vaporous at atmospheric pressure and a temperature of 60° F.

3. The process of claim 1 further characterized in that said isoparaffin is isobutane.

4. The process of claim 1 further characterized in that said olefinic feed stream comprises propylene.

5. The process of claim 1 further characterized in that said olefinic feed stream comprises butylene.

6. The process of claim 2 further characterized in that said normal paraffin is normal butane.

7. In a process for the acid-catalyzed alkylation of an isoparaffin with an olefin, the method of controlling the temperature of the reaction mixture within the alkylation reaction zone which comprises the steps of:
    a. introducing a liquefied normal paraffin hydrocarbon into said alkylation reaction zone and therein vaporizing said hydrocarbon via heat exchange means in said reaction zone in contact with said reaction mixture;
    b. sensing the temperature of said reaction mixture, comparing the sensed temperature with the predetermined temperature specified by the adjustable set point of a temperature controller and developing an output signal representing the resulting comparison; and,
    c. regulating the quantity of said liquefied hydrocarbon introduced into said alkylation reaction zone in response to said output signal.

8. The process of claim 7 further characterized in that said isoparaffin is isobutane.

9. The method of claim 7 further characterized in that said output signal of step (b) is transmitted to a flow controller, the adjustable set point of which is adjusted in response thereto, a second signal is developed representing the resulting adjustment and the quantity of said liquefied hydrocarbon is regulated responsive to said second signal.

10. A process for alkylating isobutane with an olefinic feed stream which comprises the steps of:
   a. reacting said isobutane with said olefinic feed stream, in admixture with a hydrogen fluoride catalyst, in an alkylation reaction zone, at alkylating conditions resulting in a reaction product effluent;
   b. introducing liquefied normal butane into said reaction zone and therein vaporizing said normal butane via heat exchange means in said reaction zone in contact with the reaction mixture of hydrogen fluoride, isobutane and said olefinic feed stream;
   c. sensing the temperature of said reaction mixture, comparing said temperature with the predetermined temperature specified by the adjustable set point of a temperature controller and developing a first output signal representing the resulting comparison;
   d. withdrawing vaporized normal butane from said alkylation reaction zone;
   e. increasing the pressure of said withdrawn vaporized normal butane;
   f. introducing said pressurized normal butane from step (e) along with a mixture of isobutane and normal butane into a fractionation column;
   g. removing separate streams of isobutane and normal butane from said column;
   h. liquefying at least a portion of said normal butane from step (g) and recycling said liquefied normal butane to said heat exchange means of said alkylation reaction zone;
   i. withdrawing an alkylate product from step (a), and
   j. transmitting said first output signal from step (c) to a flow controller having an adjustable set point which is adjusted responsive to said first signal, developing a second output signal representative of the resulting adjustment and regulating the quantity of said liquefied normal butane in response to said second signal.

* * * * *